United States Patent [19]

Shindo et al.

[11] Patent Number: 5,556,597
[45] Date of Patent: Sep. 17, 1996

[54] TEST STRIP SUPPLY APPARATUS

[75] Inventors: Isao Shindo; Shigeo Mutou; Susumu Kai, all of Hitachinaka; Tokio Omori, Ibaraki, all of Japan

[73] Assignee: Hitachi, Ltd., Tokyo, Japan

[21] Appl. No.: 433,569

[22] Filed: May 3, 1995

[30] Foreign Application Priority Data

May 11, 1994 [JP] Japan .................................. 6-097160

[51] Int. Cl.$^6$ ..................................................... G01N 35/00
[52] U.S. Cl. ............................. 422/63; 422/65; 422/104; 436/43; 436/46; 221/263; 221/266
[58] Field of Search ....................... 422/58, 63, 65, 422/66, 104; 436/43, 44, 46, 47, 48, 49; 435/810, 805, 809; 221/233, 263, 266

[56] References Cited

U.S. PATENT DOCUMENTS

| 4,279,514 | 7/1981 | Blümel et al. ........................... 356/445 |
| 4,876,204 | 10/1989 | Inoue et al. . | |
| 5,298,425 | 3/1994 | Huhn et al. ................................ 436/43 |
| 5,378,630 | 1/1995 | Kai et al. . | |
| 5,415,840 | 5/1995 | Sano et al. ................................. 422/67 |
| 5,460,968 | 10/1995 | Yoshida et al. ............................ 436/46 |

FOREIGN PATENT DOCUMENTS

| 542260A1 | 5/1993 | European Pat. Off. . |
| 555711A1 | 8/1993 | European Pat. Off. . |
| 597419A1 | 5/1994 | European Pat. Off. . |
| 6-148201 | 5/1994 | Japan . |

*Primary Examiner*—Long V. Le
*Attorney, Agent, or Firm*—Fay, Sharpe, Beall, Fagan, Minnich & McKee

[57] ABSTRACT

Test strip supply apparatus includes a rotatable container which has guide part materials for holding a through groove and a weight. Under a supporting table having a take-out hole for the test strip dropped from the through groove of the container, a conveyance stage is provided for receiving the test strip dropped from the through groove and transferring it. The weight facing near both ends of the through groove lets the test strip descend and prevents a surplus number of the test strips from entering the through groove.

5 Claims, 6 Drawing Sheets

TEST STRIP SUPPLY APPARATUS

BACKGROUND OF THE INVENTION

This invention relates to a test strip supply apparatus and especially relates to a test strip supply apparatus used when analyzing a sample from a living body, such as urine or blood by using a test strip impregnated with a reagent.

In a medical examination of the hospital, a test strip is often used easily to inspect several analytical items contained in an urine sample and a blood sample. The several test strips are clung with the reaction layer which impregnated the reagent on an elongate sheet-like strip which consists of plastic etc.

As a general automatic analyzer which is automated to handle such a test strip, U.S. Pat. No. 4,876,204 may be cited as an example of such apparatus. In such prior art, it is shown that an arm having a test strip gripper moves between the sample table and the photometric mechanism, and the test strip which develops color is optically measured. The sample table holds the sample container into which the test strip is dipped. The test strip supply mechanism supplies the test strips one by one to a start position for a test strip position for a test strip transportation with the arm. The test strip supply mechanism shown in U.S. Pat. No. 4,876,204 is provided with a bottom that can slide to the hopper which the test strip is cast into, and has means for supplying the test strip by movement of the bottom outside of the hopper.

In the test strip supply apparatus mentioned in U.S. Pat. No. 4,876,204, the test strip can easily be caught between a wall and a bottom of the hopper, thus decreasing reliability. In order to overcome. Such a problem, the inventors of the present invention have invented a test strip supply apparatus which has a test strip accommodation container moving to and from on a supporting table. Such example is mentioned in U.S. Pat. No. 5,378,630.

By using the apparatus mentioned in U.S. Pat. No. 5,378,630, it becomes possible to take out the test strip to the outside one by one automatically. However, this case doesn't lead to a technology to be able to supply the test strip smoothly in this example. In particular, in this example, a through groove for taking out the test strip is formed on a wall of the accommodation container, but when the test strip is dropped from the accommodation container into an accept department on a passage stage through the through groove, more than three pieces of the test strips may get into in the through groove in succession resulting in trouble. After having let one of the test strips conveyed to an outside take-out position usually, as the test strip leading to it is one or zero, it is returned into the accommodation container, and rotational motion of the accommodation container is again provided. But, those all may not come back in the accommodation container in the case that more than two pieces of the test strip remained. Therefore, the rotational motion of the accommodation container is obstructed. Further, a test strip supply apparatus which has a pushing members to push the test strips in the rotatable container into an guide member is shown in Japanese Patent Laid-Open No. 6-148201(1994).

SUMMARY OF THE INVENTION

The object of the present invention is to provide a test strip supply apparatus which repeats movements to take out elongate test strips one by one from a container accommodating test strip smoothly.

In the test strip supply apparatus comprising a container having a test strip accommodation room that could accommodate several elongate test strips having layers impregnated with a reagent, wherein a through groove is formed for taking out the test strip on a wall of the container, and supplying the test strip into a predetermined position outside of the container through the through groove from the container by making the container rotate, the present invention is characterized comprises a guide department formed in the above contains the said guide department guides one of the test strip of the above test strip accommodation room towards a direction of the above through groove, and an approach block member disposed so as to advance or retreat for the test strip introduction passage obstructs that passage when a surplus number of test strips approaches the through groove.

In a desirable embodiment of the present invention, the container is a tube type, the guide department is arranged along a inner wall surface of an elongate direction of the above container, and the approach block member is arranged in both ends neighborhood in width direction of the test strip introduction passage. The approach block member consists of a weight department material which is rotated by self-weight thereof according to the rotation of the container, a weight housing room in which the weight member moves freely to a guide department is formed and the weight members are loaded in the weight housing room. The weight housing room has an opening that faces a test strip guide passage, when the opening is moved so as to look down, a part of the weight member is protruded from the opening to the test strip guide passage.

When a reciprocating rotary motion is fed to the container which accommodates the several elongate test strip having a layer dipped reagent, many test strip in the accommodation room are moved to a direction crossed to a elongate direction of the test strip. The guide member effects to install any of the test strip in the through groove with this motion surely. In this case, the approaching test strip slides so as to pass through the test strip guide passage limited by a guide department and a wall in container, the test piece is prevented from dashing out into the outside during turning motion by a supporting board and installed in the through groove. As the approach block member does not protrude to the test strip guide passage during turning motion of the container substantially, approach of the test strip to the through groove direction is not disturbed. But, when the container is stopped in order to take Gut the test strip from container, the approach block member projects into the test strip guide passage, and surplus number of the test strip are blocked so as not to slide into the through groove during standstill of the container. Thereby, just after when the container is stopped, for example, two test strips exist in the through groove at most as a maximum allowable number. Even if the through groove is opened up for conveyance stage after the stopping of the container and the test strips are dropped in the through groove in a receipt department on said stage, and the guide department is passed through, and new test strip doesn't come into the through groove. After the test strip received in a receipt department of the stage is conveyed to a position for being taken out, a take-out port of the through groove of the container is closed, preparation of the next container rotary motion is arranged, as the number of remaining test strips which is left so as not to be conveyed is one at most, and the test strip is returned to the through groove in the container. When the test strip of surplus number should be steeped to the container side according to a closing motion of the take-out port of the through groove, the returning motion may not progress smoothly because of the thickness of the several test strip, and according to the present invention, such trouble is avoided.

In a desirable embodiment of the present invention, a weight housing room is formed by a guide portion, the weight housing room has an opening facing the test strip guide passage, and when the container is stopped and the opening thereof is moved to look down, the weight department materials partially protrude in the test strip guide passage from the opening by self-weight. Thereby, the test strip of surplus number is prevented from passing into the through groove. In the case of an example which an arrangement position of the weight member faces the through groove, when the take-out opening of the through groove is opened, as gravity of the weight member acts on the test strip on the through groove from upward, a power that the test strip is put to the conveyance stage is added, and a movement for taking out the test strip is assured still more. When the container turns and the opening of the weight housing room is disposed in a side direction, it isn't prevented by the weight member that the test strip comes in a way of the through groove because the weight member moves back to the inside of the weight housing room.

DETAILED DESCRIPTION OF THE PREFERRED EMBODIMENT

Figure 6A:
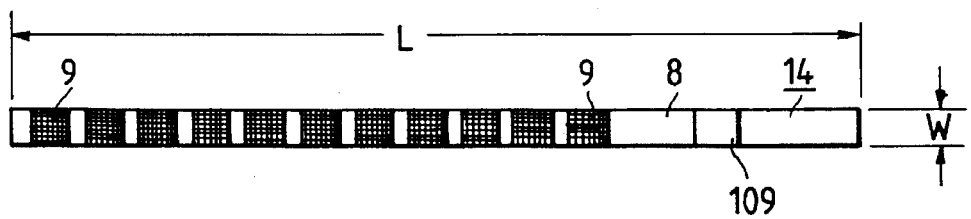
FIG. 6(A) shows a top view of a test strip example and FIGS. 6(B) and 6(C) show side views of a test strip sample respectively before and after being dipped in a sample liquid.
Figure 6B:
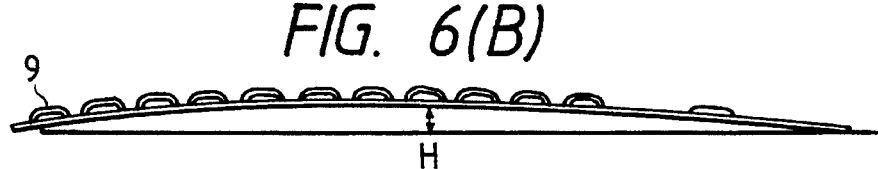
Figure 6C:
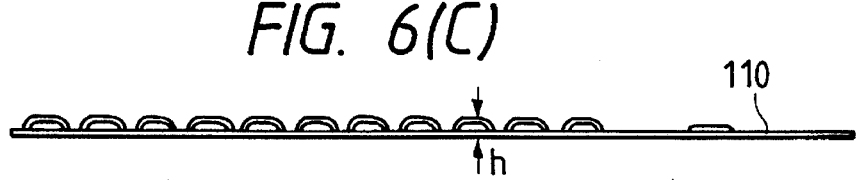

An example of the test strip is shown in FIG. 6. As shown in FIG. 6 (A), the test strip 14 is fixed with reaction layers 9 and impregnated with a reagent in stick 8. Test strip 14 consists of an elongate sheet-like plastic of length L with several nylon mesh membranes, and a mark 109 for distinguishing the right side from the wrong side were. After all of the reaction layers 9 were dipped in a sample simultaneously, they were raised from the sample liquid, and developed colors in the reaction layers. Generally, the size of each reaction layer 9 is 5 mm, and the thickness of reaction layer is 0.5–1.5 mm. The length L of the test strip 14 shown in FIG. 6 is 120 mm, and the width W thereof is 5 mm, and the height h thereof is 1.8 mm. The material of the reaction layer 9 consists of a filter paper or a felt.

The shape of the test strip 14 before dipped in the sample liquid becomes a curve of a constant height H in an elongate direction as shown in FIG. 6 (B). After being dipped in the sample liquid, it becomes linear as shown in FIG. 6 (C).

This invention is applied to an analyzer for analyzing the sample from the living body such as urine sample or blood sample, and here, an automatic analyzer applied to the urine sample is explained as an example.

Figure 7:
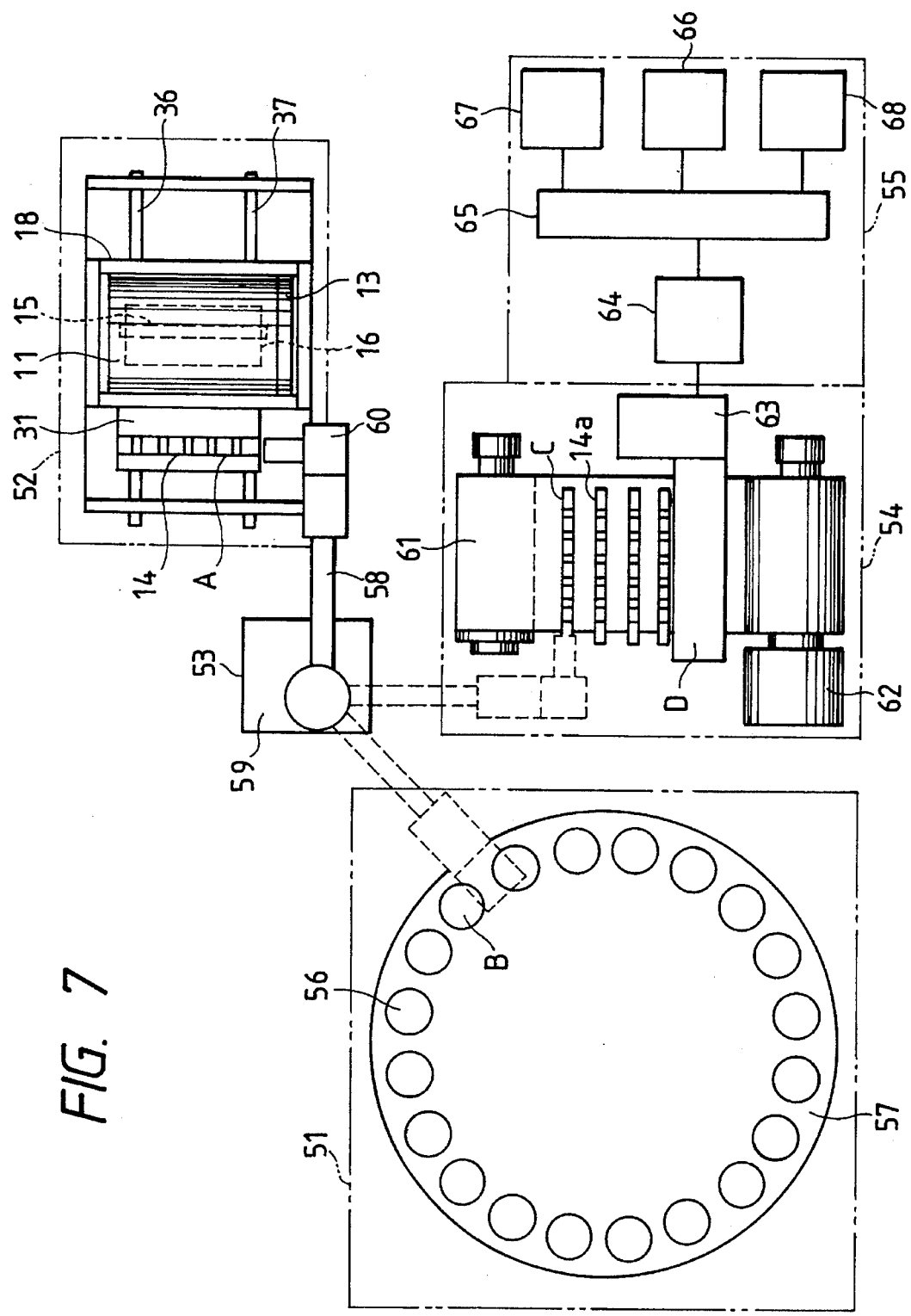
FIG. 7 shows a total constitution of an analysis apparatus as an embodiment in the present invention.

FIG. 7 shows a total constitution of an analysis apparatus for the urine sample as an embodiment in the present invention. The analyzer in FIG. 7 has an automatic supply apparatus 52, a sample positioning device 51, a test strip transportation device 53, a measurement device 54 and a control operation part 55. The control operation part 55 controls movement of each mechanism part, and the measurement data of each reaction layer of the test strip measured by photometer 63 are operated and the measurement results thereof are output.

Figure 8:
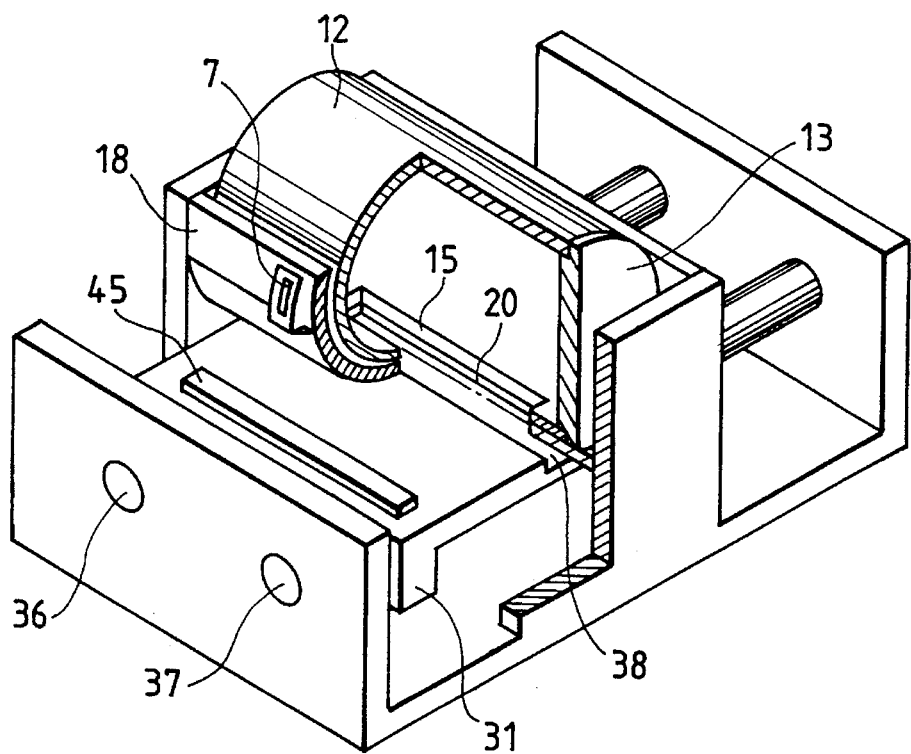
FIG. 8 show a perspective view of the apparatus shown in the FIG. 1.

A sample positioning device 51 successively transfers the sample container 56 accommodating the urine sample arranged on a turn table 57 to a position B where the test strip is dipped. The test strip automatic supply apparatus 52 supplies the test strip 14 one by one to the predetermined outside take-out position A from the cylindrical container 11 accommodating the test strips. The supply movements of the test strip to the outside take-out position A is repeated synchronously with the movement cycle of the analyzer. To an end of the cylindrical container 11, a cover 13 that gets in and out the test strip is installed. A through groove 15 for taking out the test strip is formed on a curved wall located in the most lower layer of cylindrical container 11 (Refer FIG. 8).

The guide part 16 which helps the test strip to be inserted in the through groove 15 surely is arranged so as to cover the through groove 15. A weight 70 is used as an approach block member material for blocking the entering of the test strip and is installed on the guide part 16 (Refer FIGS. 9, 10). The cylindrical container 11 is installed rotatably on a container supporting table 18 which serves to prevent material from jumping out of the test piece and a fresh air interception material. A test strip conveyance stage 31 for moving the test strip taken out from the through groove 15 to the outside take-out position A is arranged underneath of the supporting table 18, and may move on the guide axis 36, 37 so that the upper face of the conveyance stage 31 slides the under face of the supporting table 18.

The test strip transportation device 53 has an arm 58 that can be turned, a drive mechanism 59 thereof, and a test strip gripper 60 installed in a top end of the arm 58. This transportation device 53 holds the end 110 of the test strip 14 supplied to the outside take-out position A by gripper 60 (Refer FIG. 6), conveys it to the dipping position B, and dips all of the reaction layers 9 of the test strip 14 holding the end 110 of the test strip 14 in the sample in the sample container 56 disposed in the dipping position B. After having dipped a predetermined period of time, the test strip 14 is raised from the sample conveyed to the measurement device 54, and the test strip is released from the gripper 60 at a position C for placing the test strip. The gripper 60 returns to the outside take-out position A of the test strip supply apparatus 52 afterwards, and the next test strip is supplied to the outside take-out position A by this time. Such movements are repeated during the analysis processing.

A roll paper 61 is used to transfer the test strip 14a in a reaction received from the test strip maintenance conveyance device 53 in the measurement device 54.

The test strip 14a put on the position C is transported to an optical measuring position D by winding up the roll paper 61 with a winding-up mechanism 62 at predetermined time intervals. The test strip 14a is positioned at the optical measuring position D next to photometer 63 a predetermined time after being dipped in the sample. In the photometer 63, an optical source for generating a light having a specified wavelength corresponding to each analytical item and a small reflection type optically measuring part which consists of a silicon photo-diode light intercepting element are arranged corresponding to a detecting position of the each reaction layer side of the test strip 14a, and a strength of the light reflection from the each reaction layer side which reacted and colored is measured. The measurement result goes by way of an A/D conversion device 64, and is processed in a control part 65, and is indicated in liquid crystal indication device 66 and simultaneously printed out with a printer 67. Analysis works by using this apparatus are performed by an input applied from the operation panel 68. The test strip is wound up with a roll paper by mechanism 62 after finishing the measurement, and is taken out and disposed.

Figure 2:
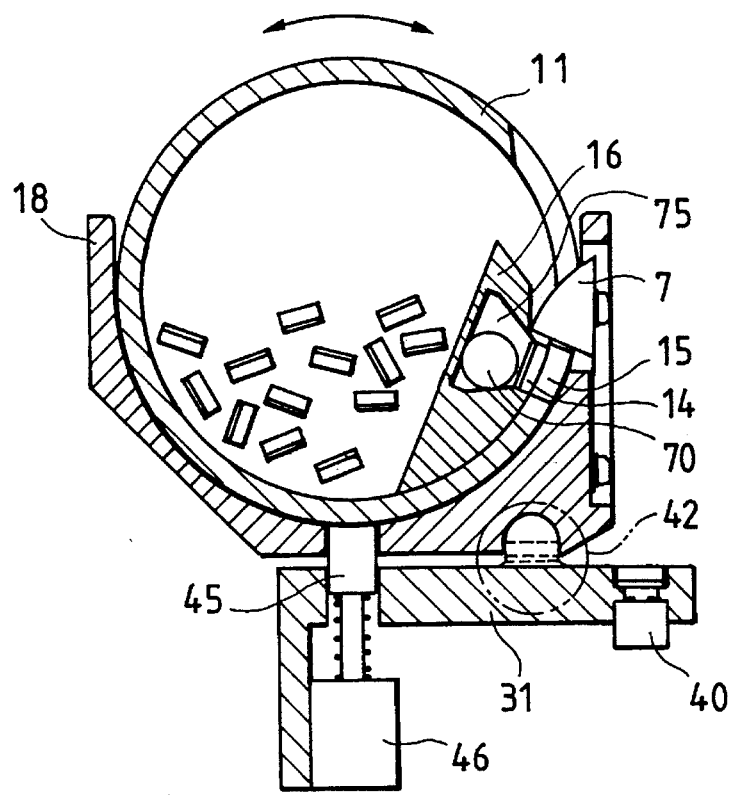
FIG. 2 is a explanatory view of movements of an apparatus shown in the FIG. 1.
Figure 3:
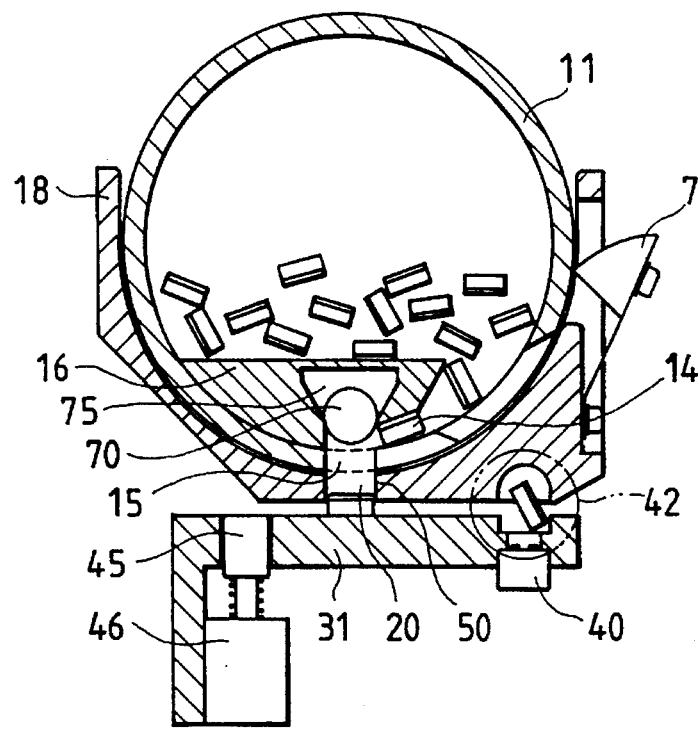
FIG. 3 is an another explanatory view of movements of an apparatus shown in the FIG. 1.
Figure 4:
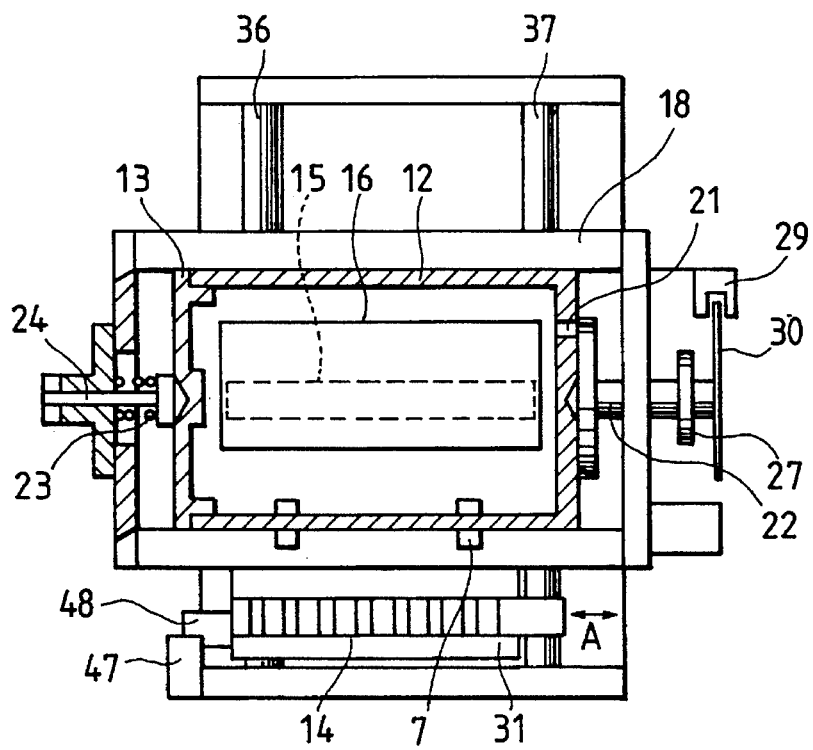
FIG. 4 is a IV—IV cross section of the apparatus shown in the FIG. 1.

The practical constitution of the test strip automatic supply apparatus 52 adopted in analyzer of FIG. 7 will be explained by using FIGS. 1 to 5 and FIGS. 8 to 10. As an example of the cylindrical container 11 that accommodates the several test strips, a cylindrical container is shown in these figures. The cylindrical container 11 has a container body 12 and a cover 13 (Refer. FIG. 4), a space between a right wall and a left wall of the container body 12 forms the test strip accommodation room and the distance therebetween, that is, the depth of the test strip accommodation room is formed considerably larger than the length L of the test strip 14. Thereby, if the test strip is fixed in a lengthwise direction, and is put into the accommodation room, and the cylindrical container 11 is reciprocally rotated, each test strip isn't disposed a various directions.

The cylindrical center becomes a rotational center.

The curved wall of the cylindrical container 11 spreads in parallel to the rotational center direction, and a rectangular through groove 15 having a size and a shape as that of the test strip to be inserted is formed. In other words, the length of the through groove 15 is bigger a few than length L of the test strip 14 and the width of the through groove 15 is bigger a few than width W of the test strip 15. And, the depth of through groove 15 is almost same as the height h of the test strip 14. The guide part 16 is formed from the through groove 15 to the rotational vecter side. The guide part 16 leads the test strip which, for example, in a clockwise direction gets into the through groove 15. But, for the test strip which is going to begin with the clock course which is against, the foot part of the guide part 16 connected to the wall side blocks other test strips from entering to the through groove 15.

The separation distance between the extended part of the guide part materials 16 and the upper edge of the through groove 15 is bigger than the height h of one piece of the test strip 14, and is smaller than 2 h which is two times of the height of test strip. Because of such construction, the test strips 14 are supplied one by one into the through groove 15.

Figure 9:
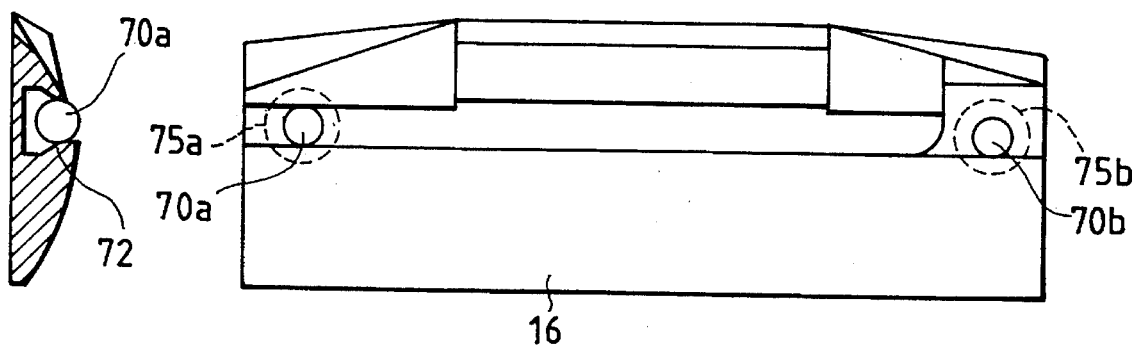
FIG. 9 is a figure of detail constitution of the guide portion.
Figure 10:
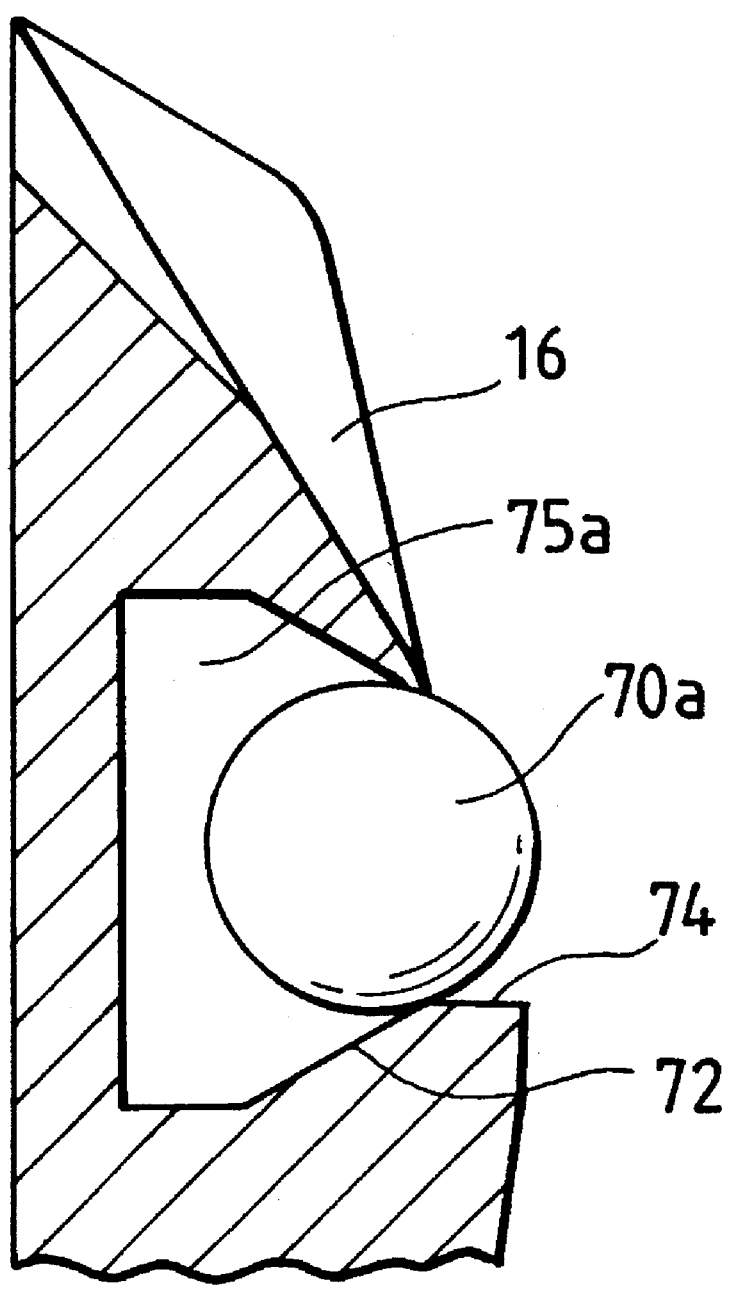
FIG. 10 is a partial expansion cross section of the guide portion of FIG. 9.

Referring to FIGS. 9, 10, the guide part 16 will be explained as follows. The guide part 16 is formed in the container 11 and the width flat direction thereof is arranged in parallel to a rotational center axis of the container 11. The width of the guide part 16 is almost same as the length L of the test strip 14. Weight accommodating rooms 75a, 75b having the same shape are respectively formed near both ends in the width direction in the guide part 16 arranged along a wall side disposed in a lengthwise directions of container 11. Spherical weight members 70a, 70b having a gravity of more than 2.5 are accommodated in these accommodating rooms 75a, 75b. The accommodating rooms 75a, 75b are so large that the weight members can move freely. The accommodating room 75a, 75b has a slant side 72 of a circular cone shape and an opening part 74. The size of the opening part 74 is formed smaller than a diameter of the weight member 70a, 70b and the weight member is prevented from falling out. When the opening part 74 is positioned downward in the case the container 11 stopped, the weight member 70a, 70b is protruded from the opening part 74, and is guided by the slant side 72. When the container 11 rotates and the opening part 74 faces to the side, the weight member 70a, 70b enters inside of the accommodating room 75a, 75b according to its own weight, and entry of the test strip becomes easy (Refer FIG. 2). These weight members 70a, 70b are arranged so as to be just above the elongate through groove 15.

Figure 5:
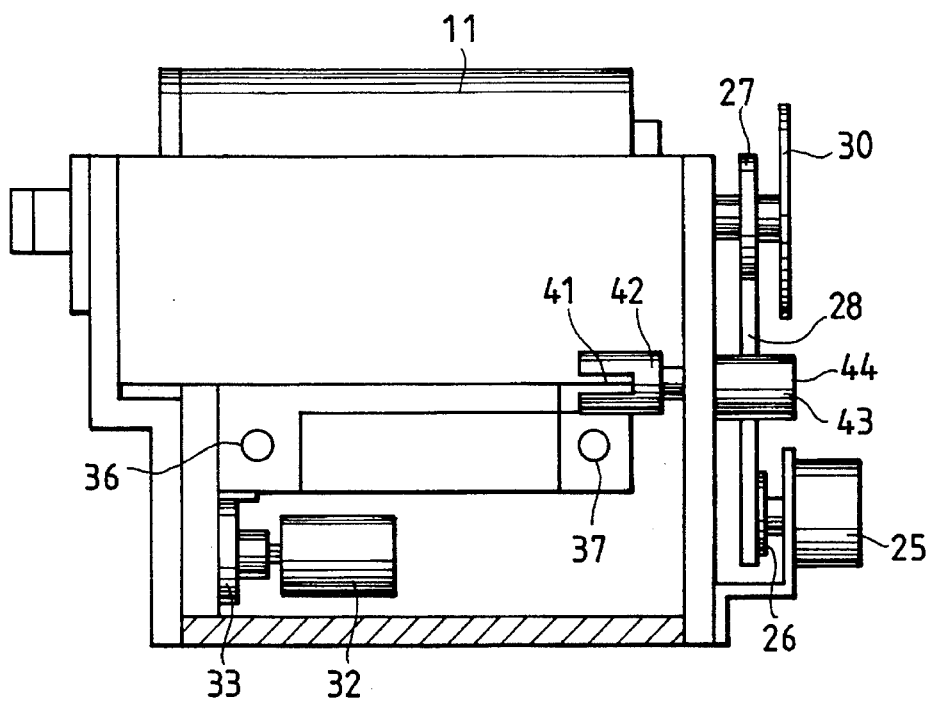
FIG. 5 is a front view of the apparatus shown in the FIG. 1.

As shown in FIGS. 4 or 5, the cylindrical container 11 is reciprocally rotated by a pulse motor 25, but the rotational angle of reciprocal rotation of such container 11 is controlled by a control part 65 based on signals supplied from a circle board 30 with a notch arranged in the rotational axis 22 of a rotational force transmission mechanism and a notch position detector 29 installed on the supporting table 18. The rotational angle of the reciprocal rotation of the cylindrical container 11 is more than 30 degrees in both the clock-wise direction and the counterclock-wise. When rotated more than the angle, the test strip in the container moves along the curved wall easily.

One side end of the cylindrical container 11 is fitted with a projection 21 for power communication of rotational power communication mechanism (Refer FIG. 4). As the cover 13, being on the other side end of the cylindrical container 11 is supported by a support axis 24 having a spring 23, the connection between the container body 12 and the projection 21 is removed by pushing the container body 12 to the left side of the FIG. 4 and the container 11 is taken out from upward. Only one through groove is formed in the cylindrical container 11 in an example of the figure, two or more through grooves may be formed as needed.

The outside surface in the length-wise direction of the cylindrical container 11 is formed so as to slide on the curved inside surface of the container supporting table 18. This container supporting table 18 prevents the through groove 15 from being opened up to the outside during the rotational movement of the container 11. If the through groove 15 were opened up to the outside temporarily, the test strip would be thrown out from the through groove 15. Therefore, the supporting table 18 covers the whole space where the trough groove moves to in turn movements thereof, and is arranged to prevent the test strip from jumping out from the through groove.

Figure 1:
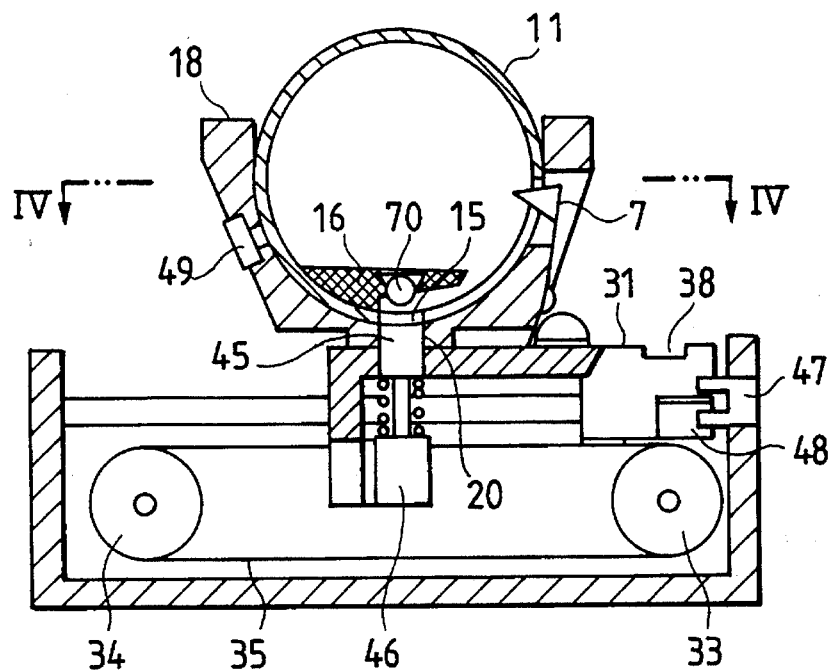
FIG. 1 is a sectional view of the test strip supply apparatus applied to the present invention.

The supporting table 18 as a jump-out prevention materials for the test strip covers a lower side surface of the cylindrical container 11 also, but the test strip needs to be taken out from a lower side. Thus, in a predetermined position of the supporting table 18 corresponding to the through groove 15 when the rotational movement of the cylindrical container 11 is stopped, a hole 20 for passing the test strip from the through groove 15 to the conveyance stage 31 (Refer FIGS. 1, 8) are formed. This hole 20 is closed with a closing material 45 as shown in FIG. 2 while the cylindrical container 11 rotates, and is opened as shown in FIG.

3 when the test strip descends from the container. The test strip while descends is loaded with a test strip receipt ditch 38 top formed on the test strip conveyance stage 31 that slides to move to, and is conveyed afterwards to the position A. Length and width of the receipt ditch 38, too are formed so as to fit to the size of the test strip 14. The side wall materials of the container supporting table 18 supports the rotational power communication mechanism. The hole 20 is formed at a center part of the curved inner wall of the half cylindrical shape of the supporting table 18. The cylindrical container 11 for the test strip is made of a transparent material, for example, acrylic acid resin. The supporting table 18 shown in the figure is formed so that the reciprocal rotational angle of the cylindrical container can be rotated up to 90 degrees in the clockwise and counterclock-wise directions, and an upward portion of the supporting table is opened so as to pull out the cylindrical container 11.

The cylindrical container 11 is supported by a movable support axis 24 having a spring 23 for pushing the touch support axis 22 and the container having a projection 21 for rotational power communication in an axial direction.

The rotational power for the cylindrical container 11 is given by a pulse motor 25, pulleys 26,27, a timing belt 28, and the rotational angle is detected by the detector 29 and the rotational circle board 30 having the notch on the circumference thereof and is controlled.

The test strip conveyance stage 31 reciprocally moves to a horizontal direction along the guide axis 36,37 by the motor 32 (FIG. 5), the pulley 33,34 (FIG. 1) and the timing belt 35. The detector 40 for detecting the right side or the wrong side of the test strip optically (FIG. 2) are provided at the lower side of the ditch 38 for receiving the test strip. And, a rotational body 42 having the ditch 41 is provided facing the passage of the conveyance stage 31. Turning over mechanism 44 has the motor 43 for driving the rotational body 42 and itself (FIG. 5). The function for turning over the test strip so as to arrange the test strip in the right side is provided, thereby the rotational body 42 doesn't move rotationally in case of the right side for the test strip 14, and the rotational body 42 is turned by 180 degrees when the handle part 110 of the test strip is located in the ditch 41 in case of the wrong side for the test strip 14.

As the ditch 41 of the turn body 42 is not co-axial with the turn axis, the curved test strip is surely fitted to the ditch 41 in case of the right side or the wrong side for the test strip.

A shutter 45 (FIGS. 1, 2) is provided so as to open and shut the hole 20 for taking out the test strip on the container supporting table 18 and actuated by the solenoid 46. The detector 47 and a detection terminal 48 shown in FIG. 1 are provided for deciding the stop position of the conveyance stage 31.

In this embodiment, the number of test strips which are loaded at a time in the cylindrical container 11 is 200. The test strip supply apparatus in the present invention starts with a situation as shown in FIG. 1. That is, the cylindrical container 11 mounted and the hole 20 of the container supporting table 18 is closed by the shutter 45, and works in the following procedure.

(1) The pulse motor moves, thereby make the cylindrical container 11 rotate reciprocally. The test strip 14 is pushed in a passage under the guide part 16. A claw is held by a leaf spring and provided so as to be pushed or pulled through a thin gap. Because the weight 70 gets into the accommodating room 75 the weight 70 doesn't become obstruction, and passes one of the test strip in the through groove 15. Rotating reciprocally more than 90 degrees in this embodiment to the right or the left, the test strip is surely fitted in the through groove 15, and the detector 49 is provided for the confirmation (Refer FIG. 1).

(2) In a state that the through groove 15 of the cylindrical container 11 corresponds to the hole 20 of the container supporting table 18, the shutter 45 is pushed towards the lower side, thereby the hole 20 is opened, and the test strip moves down on the conveyance stage 31. The next test strip comes in the guide part 16, but as the weight member 70 blocks up an exit as shown in FIG. 3, the test strip does not fall by vibration. And, the test strip which should be dropped down comes down stably without being pushed by the next test strip.

(3) The conveyance stage 31 is moved to a retreat direction (the left direction of the FIG. 1) , thereby the test strip receipt ditch 38 is disposed a position under the hole 20, and the test strip that is moved down is dropped in to the ditch 38 so as to be fitted.

(4) The conveyance stage 31 is moved to a progress direction (the right direction of the FIG. 1), and the test strip is transported to the outside take-out position A.

(5) While the test strip is transported, the right side or the wrong side of test strip is judged by the detector 40, the right side and the wrong side turning over mechanism 44 turns the test strip when necessary (Refer FIG. 3).

(6) When the test strip is positioned in the outside take-out position A, the shutter mechanism returns to a position corresponding to the hole 20, the test strip remaining by the operation of the solenoid 46 is pushed up and is returned in the container 11, and the hole 20 is closed at the same time, and the function S of the above step (1) are started again.

By repeating the above-mentioned steps, the curved test strips which are loaded in the cylindrical container 11 begin to be transported to the outside take-out position automatically in sequence. When the apparatus in this embodiment is used as the urine automatic analyzer, this apparatus can supply the test strip with a speed of one strip every 12 seconds.

In the embodiment mentioned above, the weight member is shown as a spherical thing, the shape thereof isn't always limited to the above and even a column shaped, semicircle spherical thing may be used. The test strip curves in the length direction as shown in the FIG. 6 (B) and a guide department is shaped as in FIGS. 9, 10, and the test strip may be transported to the stage smoothly.

According to this invention, as the surplus number of the test strips are not transported to the through groove, and repetitive motions as the start and stop of the rotation of the container are proceed smoothly, a continuous driving to supply the test strip in the predetermined position one by one is executed surely.

We claim:

1. A test strip supply apparatus comprising a container having a test strip accommodation room for accommodating a plurality of elongate test strips having a reagent dipping layer, and a through groove, for taking out the test strips, formed on a wall of the container, wherein said test strip supply apparatus supplies the test strips from said container to a predetermined position outside of the container through the through groove by rotating the container, said test strip supply apparatus comprising, a guide part formed in the container for bringing one of the plurality of test strips in the test strip accommodation room into the through groove, and an approach block member positioned in said guide part and arranged so as to protrude or retreat in a test strip guide passage by rotation of said container, said approach block member preventing more than said one of the test strips from passing through the through groove at a given time.

2. A test strip supply apparatus as defined in claim 1, wherein said container is cylindrical, said guide part is arranged along an inner surface of the container in a longitudinal direction thereof, and said approach block member is arranged adjacent both ends in a perpendicular direction of said test strip guide passage.

3. A test strip supply apparatus as defined in claim 1, wherein said approach block member has a weight member which moves according to the rotation of the container, and said guide part forms a weight accommodating room therein in which the weight member moves freely.

4. A test strip supply apparatus as defined in claim 3, wherein said weight accommodating room has an opening facing the test strip guide passage, and at least a part of said weight member protrudes in the test strip guide passage from the opening when the opening is turned downwards.

5. A test strip supply apparatus as defined in claim 1, wherein said approach block member is arranged facing the through groove.

* * * * *